US010106477B2

(12) United States Patent
Fenlon et al.

(10) Patent No.: US 10,106,477 B2
(45) Date of Patent: Oct. 23, 2018

(54) PROCESS FOR PREPARING 1,4-BIS(ETHOXYMETHYL)CYCLOHEXANE

(71) Applicant: BASF SE, Ludwigshafen am Rhein (DE)

(72) Inventors: Thomas Fenlon, Mannheim (DE); Stefan Rüdenauer, Weinheim (DE); Ralf Pelzer, Fürstenberg (DE); Shrirang Hindalekar, Mumbai (IN); Vijay Narayanan Swaminathan, Ludwigshafen (DE); Nitin Gupte, Thane (IN); Sadanand Ardekar, Kalyan East (IN)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 15/753,236

(22) PCT Filed: Aug. 17, 2016

(86) PCT No.: PCT/EP2016/069487
§ 371 (c)(1),
(2) Date: Feb. 16, 2018

(87) PCT Pub. No.: WO2017/029312
PCT Pub. Date: Feb. 23, 2017

(65) Prior Publication Data
US 2018/0237369 A1  Aug. 23, 2018

(30) Foreign Application Priority Data
Aug. 18, 2015  (EP) .................................. 15181402

(51) Int. Cl.
C07C 41/01 (2006.01)
C07C 43/115 (2006.01)

(52) U.S. Cl.
CPC ............ *C07C 41/01* (2013.01); *C07C 43/115* (2013.01); *C07C 2531/02* (2013.01); *C07C 2601/14* (2017.05)

(58) Field of Classification Search
CPC ..... C07C 43/115; C07C 41/01; C07C 43/162; C07C 43/1781; C07C 29/44; C07C 41/16; C07C 2601/14; C07C 2531/02; C11B 9/0034; A23L 27/203
See application file for complete search history.

(56) References Cited

FOREIGN PATENT DOCUMENTS

| JP | H11029512 A | 2/1999 |
|---|---|---|
| JP | H11035969 A | 2/1999 |
| WO | WO-2013004579 A2 | 1/2013 |

OTHER PUBLICATIONS

Freedman, H, et al., "An Improved Williamson Ether Synthesis Using Phase Transfer Catalysis", Tetrahedron Letters, vol. 16, No. 38, (1975), pp. 3251-3254.
International Search Report for PCT/EP2016/069487 dated Oct. 12, 2016.
Juršić, B., "Synthetic Application of Micellar Catalysis. Williamson's Synthesis of Ethers", Tetrahedron, vol. 44, No. 21, (1988), pp. 6677-6680.
Solladie, G., et al., "A New Class of Chiral Smectic Liquid Crystals: Substituted Biphenylylcyclohexylideneethanones Having an Axial Chirality", Journal of Organic Chemistry, vol. 50, No. 21, (1985), pp. 4062-4068.
Written Opinion of the International Searching Authority for PCT/EP2016/069487 dated Oct. 12, 2016.
International Preliminary Report On Patentability with Written Opinion for International Application No. PCT/EP2016/069487, dated Feb. 20, 2018.

*Primary Examiner* — Jafar F Parsa
(74) *Attorney, Agent, or Firm* — Drinker Biddle & Reath LLP

(57) ABSTRACT

The present invention relates to a process for preparing, 4-bis(ethoxymethyl)cyclohexane, which comprises reacting 1,4-bis(hydroxymethyl)cyclohexane with ethyl chloride in the presence of an inorganic base, a solvent and a phase transfer catalyst to yield a reaction mixture containing 1,4-bis(ethoxymethyl)cyclohexane, where the inorganic base is selected from alkali metal hydroxides and earth alkaline metal hydroxides and where the solvent is selected from water or a mixture of water with at least one organic solvent.

14 Claims, No Drawings

PROCESS FOR PREPARING 1,4-BIS(ETHOXYMETHYL)CYCLOHEXANE

CROSS-REFERENCE TO RELATED APPLICATIONS

This application is a national stage application (under 35 U.S.C. § 371) of PCT/EP2016/069487, filed Aug. 17, 2016, which claims benefit of European Application No. 15181402.7, filed Aug. 18, 2015, both of which are incorporated herein by reference in their entirety.

The present invention relates to a process for preparing 1,4-bis(ethoxymethyl)cyclohexane, which comprises reacting 1,4-bis(hydroxymethyl)cyclohexane with ethyl chloride.

BACKGROUND OF THE INVENTION 1,4-bis(ethoxymethyl)cyclohexane is a known fragrance chemical exhibiting favorable organoleptic properties, in particular a pleasant odor. 1,4-bis(ethoxymethyl)cyclohexane is therefore of great interest as fragrance for example in the field of cosmetics or in the field of laundry and cleaning detergents.

There is a demand for novel processes that allow the efficient production of 1,4-bis(ethoxymethyl)cyclohexane, e.g. by making use of mild reaction conditions to improve the yield and reduce the formation of unwanted by-products.

The synthesis of mono and di-ethers of 1,4-bis(hydroxymethyl)cyclohexane, including 1,4-bis(ethoxymethyl)cyclohexane, was frequently described in the art.

JP-11035969 A for example describes 4-(alkoxymethyl)-1-(hydroxymethyl)-cyclohexanes and a process for their preparation, which comprises the reaction of 1,4-bis(hydroxymethyl)cyclohexane with an alkyl, cycloalkyl or alkenyl halide in the presence of a base, in particular sodium hydride, and a solvent, in particular THF.

JP-11029512 A describes 4-(alkoxymethyl)-1-(hydroxymethyl)cyclohexanes and a process for their preparation, which comprises either the reaction of 1,4-bis(hydroxymethyl)cyclohexane with an alkyl, cycloalkyl or alkenyl halide in the presence of a base, in particular sodium hydride in THF, or the reaction of 1,4-bis(hydroxymethyl)cyclohexane with an olefin in the presence of a strong acid, in particular sulfuric acid in combination with boron trifluoride ether complex.

Solladie et al., Journal of Organic Chemistry, 1985, Vol. 50(21), pp. 4062-4068, for example describe a process for the production of 1,4-bis(ethoxymethyl)cyclohexane, which comprises the reaction of 1,4-bis(hydroxymethyl)cyclohexane with ethyl iodide in the presence of sodium hydride in THF. The alkylation reaction is performed under reflux for 16 hours to yield 30% of 4-(ethoxymethyl)-1-(hydroxymethyl)cyclohexane and 32% of 1,4-bis(ethoxymethyl)cyclohexane.

WO 2013/4579 A2 describes a process for the synthesis of 1,4-bis(ethoxymethyl)cyclohexane, which comprises the reaction of 1,4-bis(hydroxymethyl)cyclohexane in the presence of potassium hydroxide with acetylene followed by the catalytic hydrogenation of the thus obtained di-vinyl ether with hydrogen in the presence of a hydrogenation catalyst.

Freedman et al., Tetrahedron Letters, 1975, No. 38, pp. 3251-3254, for example describe the preparation of ethers from sterically less demanding mono-alcohols as well as from sterically less demanding 1,4-butandiol by reacting them with an excess of primary alkyl chlorides or benzyl chloride in the presence of an 50% aqueous sodium hydroxide solution and 3-5 mol-% of tetrabutylammonium bisulphate as phase transfer catalyst. Alkylation of sterically demanding —CH$_2$—OH groups bound to cycloaliphatic moieties were not described.

It is apparent form the state of the art, that the preparation of di-ethers of 1,4-bis(hydroxymethyl)cyclohexane is challenging. The known synthetic processes, which aim for the production of 1,4-bis(ethoxymethyl)cyclohexane through the direct alkylation of 1,4-bis(hydroxymethyl)cyclohexane, typically require highly reactive and expensive bases, such as sodium hydride, and/or suffer from moderate yields, since the alkylation reactions do often not proceed to completion, resulting in the formation of significant amounts of the mono-ether species. If harsh reaction conditions are applied, e.g. reaction conditions used in classical ether synthesis, in order to improve the yield of the di-ether species, the formation of unwanted by-products, which may have malodorous properties, is often increased.

SUMMARY OF THE INVENTION

It is therefore an object of the present invention to provide an improved process for the production of 1,4-bis(ethoxymethyl)cyclohexane from the readily available 1,4-bis(hydroxymethyl)cyclohexane in high yield and selectivity. The process should be simple and efficient by making use of mild reaction conditions to avoid the formation of unwanted by-products and thus laborious purification procedures. Furthermore, the use of highly flammable and/or expensive reagents should be avoided.

It was surprisingly found, that 1,4-bis(ethoxymethyl)cyclohexane can be prepared in high yield and selectivity by reacting 1,4-bis(hydroxymethyl)cyclohexane with ethyl chloride in the presence of an inorganic base, a solvent and a phase transfer catalyst. Therefore, the present invention relates to a process for preparing 1,4-bis(ethoxymethyl)cyclohexane, which comprises reacting 1,4-bis(hydroxymethyl)cyclohexane with ethyl chloride in the presence of an inorganic base, a solvent and a phase transfer catalyst to yield a reaction mixture containing 1,4-bis(ethoxymethyl)cyclohexane, where the inorganic base is selected from alkali metal hydroxides and earth alkaline metal hydroxides and where the solvent is selected from water or a mixture of water with at least one organic solvent.

The present process exhibits the following advantages:

- 1,4-bis(ethoxymethyl)cyclohexane can be directly produced in high yield and selectivity from the cheap and readily available starting material 1,4-bis(hydroxymethyl)cyclohexane.
- The present process uses mild reaction conditions, which reduces the amount of by-products.
- The work-up of the 1,4-bis(ethoxymethyl)cyclohexane containing reaction mixture and the purification of the crude 1,4-bis(ethoxymethyl)cyclohexane, if required, is simple and the obtained 1,4-bis(ethoxymethyl)cyclohexane can directly be used as fragrance material. Laborious work-up and purification procedures can thus be avoided.
- 1,4-bis(ethoxymethyl)cyclohexane can be synthetically produced without having to use highly flammable and/or expensive reagents such as sodium hydride.
- The process for producing 1,4-bis(ethoxymethyl)cyclohexane is simple and efficient. 1,4-bis(ethoxymethyl)cyclohexane can therefore be provided without difficulty on industrial scales.

DETAILED DESCRIPTION 1,4-bis(ethoxymethyl)cyclohexane is a compound of the following formula (I):

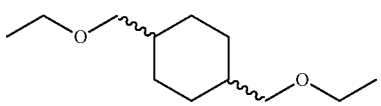

It is apparent from formula (I) that 1,4-bis(ethoxymethyl)cyclohexane can be present either in the form of cis 1,4-bis(ethoxymethyl)cyclohexane or trans 1,4-bis(ethoxymethyl)cyclohexane or in the form of mixtures of cis 1,4-bis(ethoxymethyl)cyclohexane and trans 1,4-bis(ethoxymethyl)cyclohexane.

The term "1,4-bis(ethoxymethyl)cyclohexane" encompasses both the pure cis-isomer and the pure trans-isomer, as well as mixtures, wherein these isomers are present in equal amounts or wherein one of these isomers is present in excess.

Frequently, 1,4-bis(ethoxymethyl)cyclohexane is present in the form of mixtures of cis 1,4-bis(ethoxymethyl)cyclohexane and trans 1,4-bis(ethoxymethyl)cyclohexane, wherein these isomers are present in equal amounts or wherein one of these isomers is present in excess. If desired, the (cis/trans)-isomer ratio in these mixtures can be further modified via partial or complete removal of one of the isomers using suitable purification methods, e.g. distillation, resulting in 1,4-bis(ethoxymethyl)cyclohexane isomer mixtures having a (cis/trans)- or (trans/cis)-isomer ratio of at least 70:30, preferably of at least 80:20, in particular of at least 90:10 or higher, e.g. of 95:5 or 99:1.

However, the specific isomer composition of 1,4-bis(ethoxymethyl)cyclohexane is not of particular importance for the process of the present invention.

The above definition regarding the configuration of 1,4-bis(ethoxymethyl)cyclohexane also applies for 1,4-bis(hydroxymethyl)cyclohexane, which is used as the starting material in the present process. Hence, the term "1,4-bis(hydroxymethyl)cyclohexane" encompasses both the pure cis-isomer and the pure trans-isomer, as well as mixtures, wherein these isomers are present in equal amounts or wherein one of these isomers is present in excess.

Generally, the configuration of the 1,4-bis(ethoxymethyl)cyclohexane obtained by the present process is determined by the configuration of the starting material 1,4-bis(hydroxymethyl)cyclohexane. An isomerization is typically not observed during the process of the present invention. For example, if pure cis 1,4-bis(hydroxymethyl)cyclohexane is used as the starting material the 1,4-bis(ethoxymethyl)cyclohexane is obtained as pure cis isomer. Hence, using the process of to the present invention, the cis- and trans-isomers of 1,4-bis(ethoxymethyl)cyclohexane as well as mixtures of these isomers can be prepared.

1,4-bis(hydroxymethyl)cyclohexane can either be purchased as pure cis- or trans-isomers or as cis/trans-isomer mixtures, as defined above, or can be synthesized according to procedures that are well known to the skilled person. For example, 1,4-bis(hydroxymethyl)cyclohexane can be prepared on technical scales via the catalytic hydrogenation of dimethyltherephthalate. The thus obtained 1,4-bis(hydroxymethyl)cyclohexane is often present as a mixture of cis/trans-isomers, where the cis/trans-isomer ratio largely depends on the catalyst used for the catalytic hydrogenation reaction. For example, if copper-chromite is used as the catalyst in the hydrogenation reaction the trans isomer of 1,4-bis(hydroxymethyl)cyclohexane is usually obtained in excess, whereas in the case of Ru—Sn based catalysts the cis-isomer of 1,4-bis(hydroxymethyl)cyclohexane is typically the major isomer present in the isomer mixture.

To this end, 1,4-bis(hydroxymethyl)cyclohexane is reacted with ethyl chloride in the presence of an inorganic base, a solvent and a phase transfer catalyst.

According to the present invention the inorganic base is typically selected from alkali metal hydroxides and earth alkaline metal hydroxides.

Suitable alkali metal hydroxides are by way of example lithium hydroxide, sodium hydroxide, potassium hydroxide, rubidium hydroxide and cesium hydroxide.

Suitable earth alkaline metal hydroxides are by way of example strontium hydroxide and barium hydroxide.

Preferably, the inorganic base is selected from alkali metal hydroxides, in particular from sodium hydroxide and potassium hydroxide.

In the process of the present invention, the inorganic base, with respect to the amount of OH$^-$, is typically used in an at least two-fold molar excess over the 1,4-bis(hydroxymethyl)cyclohexane present in the reaction mixture.

Preferably, the molar ratio of OH$^-$ in the inorganic base to 1,4-bis(hydroxymethyl)cyclohexane is in the range of 2:1 to 20:1, more preferably in the range of 2:1 to 15:1, in particular in the range of 3:1 to 7:1.

In a preferred embodiment of the present invention, the inorganic base is used in the form of an aqueous solution. The concentration of the inorganic base in the aqueous solution is preferably in the range of 5 to 50% by weight, more preferably in the range of 15 to 45% by weight, in particular in the range of 20 to 40% by weight.

According to the process of the present invention, the reaction is carried out in the presence of a solvent. Typically, the solvent is selected from water or a mixture of water with at least one organic solvent.

If the solvent is selected from mixtures of water with at least one organic solvent, it is preferred that the organic solvent is selected from inert organic solvents. The expression "inert organic solvent" generally means an organic solvent, which under the prevailing reaction conditions does not enter into any reactions with the starting materials or reagents participating in the reaction, or with the resultant products.

Suitable inert organic solvents that may be used together with water include, but are not limited to the following groups:
  group S1: aliphatic and alicyclic hydrocarbons, in particular alkanes and cycloalkanes having 5 to 12 carbon atoms and mixtures of these alkanes and cycloalkanes, such as pentane, hexane, heptane, octane, ligroin, petrol ether or cyclohexane;
  group S2: aromatic hydrocarbons, such as benzene, toluene, xylenes, ethylbenzene or tetralin, and mixtures thereof;
  group S3: aliphatic and alicyclic ethers, such as methyl-tert.-butylether, dibutyl ether, tetrahydrofurane, 1,4-dioxane or 1,2-dimethoxyethane;
as well as mixtures of the aforementioned solvents.

Preferably, the inert organic solvent that may be used together with water is selected from aliphatic hydrocarbons and solvents of the groups S2 and S3, as well as mixtures thereof.

More preferably, the inert organic solvent that may be used together with water is selected from solvents of the group S3, in particular from THF and 1,2-dimethoxyethane, as well as mixtures thereof.

In a preferred embodiment of the present invention, the solvent comprises at least 50% by weight, preferably at least 65% by weight, more preferably at least 80% by weight of water, based on the total amount of the solvent.

In an even more preferred embodiment of the present invention, the solvent comprises at least 90% by weight, for example 95, 98 or 99% by weight of water, based on the total amount of the solvent.

In a particularly preferred embodiment of the present invention, the solvent is selected from water.

According to the process of the present invention, the reaction is carried out in the presence of a phase transfer catalyst.

A phase transfer catalyst is a compound, which facilitates the migration of a reactant from one phase, typically the water phase, into another phase, where the reaction occurs, typically the organic phase. In the case of the present invention, the phase transfer catalyst has the function of a detergent, which increases the solubility of ionic reagents, e.g. the $OH^-$ ions present in the water phase, in the organic phase and/or the solubility of organic reactants, e.g. 1,4-bis(hydroxymethyl)cyclohexane and/or the ethyl chloride, in the water phase, thereby facilitating the alkylation reaction.

Suitable phase transfer catalysts that can be used in the process of the present invention are for example quaternary ammonium salts and phosphonium salts.

Typically, the phase transfer catalyst used in the process of the present invention is selected from quaternary ammonium salts.

In a preferred embodiment of the present invention, the phase transfer catalyst is selected from quaternary ammonium salts of the general formulae (II.a) and (II.b), $$\left[ \begin{array}{c} R^1 \\ | \\ R^1-N^+-R^2 \\ | \\ R^1 \end{array} \right]_n [Y]_{n/m}^{m-} \quad \text{(II.a)}$$

$$\left[ \begin{array}{c} R^1 \\ | \\ R^1-N^+-R^1 \\ | \\ R^1 \end{array} \right]_n [Y]_{n/m}^{m-} \quad \text{(II.b)}$$

in which
$R^1$ are independently of one another selected from unbranched or branched $C_1$-$C_{10}$-alkyl, where two adjacent radicals $R^1$, together with the nitrogen atom to which they are bonded, may also form a saturated ring having 4 to 10 carbon atoms,
$R^2$ is selected from unbranched or branched $C_1$-$C_{20}$-alkyl, $C_5$-$C_6$-cycloalkyl or benzyl,
$[Y]^{m-}$ is an m-valent single or multiatomic anion, where m has values of 1, 2 or 3, and
n has values of 1, 2 or 3.

Preferred anions $[Y]^{m-}$ are selected from halides, pseudohalides, sulfates, sulfonates, phosphates and hydroxide.

Preferred halides are for example fluoride, chloride, bromide or iodide.

Preferred pseudohalides are for example $BF_4^-$, $PF_6^-$, $CN^-$, $SCN^-$ or $OCN^-$.

Preferred sulfates are for example $SO_4^{2-}$ or $HSO_4^-$.

Preferred sulphonates are for example $CH_3SO_3^-$, $CF_3SO_3^-$, $CH_3CH_2SO_3^-$ or p-toluene sulfonic acid.

Preferred phosphates are for example $PO_4^{3-}$, $HPO_4^{2-}$ and $H_2PO_4^-$.

Particularly preferred anions are $Cl^-$, $Br^-$, $I^-$, $OH^-$, $HSO_4^-$ and $CH_3SO_3^-$.

Preferred phase transfer catalysts of the general formulae (II.a) and (II.b) are for example selected from
benzyltrimethylammonium chloride, -bromide, -iodide, -hydroxide or -hydrogen sulfate; benzyltriethylammonium chloride, -bromide, -iodide, -hydroxide or -hydrogen sulfate; hexadecyltrimethylammonium chloride, -bromide, -iodide, -hydroxide or -hydrogen sulfate;
methyltrioctylammonium chloride, -bromide, -iodide, -hydroxide or -hydrogen sulfate; tetramethylammonium chloride, -bromide, -iodide, -hydroxide or -hydrogen sulfate; tetraethylammonium chloride, -bromide, -iodide, -hydroxide or -hydrogen sulfate; tetra-n-butylammonium chloride, -bromide, -iodide, -hydroxide or -hydrogen sulfate.

In an even more preferred embodiment of the present invention, the phase transfer catalyst is selected from tetraalkylammonium salts of the general formulae (II.b), where all $R^1$ radicals are identical and selected from $C_1$-$C_{10}$-alkyl. These tetra-($C_1$-$C_{10}$-alkyl)ammonium salts are by way of example selected from
tetramethylammonium chloride, -bromide, -iodide, -hydroxide or -hydrogen sulfate; tetraethylammonium chloride, -bromide, -iodide, -hydroxide or -hydrogen sulfate; tetra-n-butylammonium chloride, -bromide, -iodide, -hydroxide or -hydrogen sulfate.

In a particularly preferred embodiment of the present invention, the phase transfer catalyst is selected from tetra-n-butylammonium salts, such as tetra-n-butylammonium chloride, tetra-n-butylammonium bromide, tetra-n-butylammonium iodide or tetra-n-butylammonium hydrogen sulfate.

Typically, the amount of the phase transfer catalyst used in the process of the present invention is in the range of 1 to 20 mol-%, preferably in the range of 2 to 15 mol-%, in particular in the range of 3 to 10 mol-%, based on the amount of 1,4-bis(hydroxymethyl)cyclohexane in the reaction mixture.

The alkylation reaction can take place in the absence of or in the presence of an inert gas. The expression "inert gas" generally means a gas, which under the prevailing reaction conditions does not enter into any reactions with the starting materials, reagents, or solvents participating in the reaction, or with the resultant products. Examples of inert gases are $N_2$, $CO_2$ and noble gases like He, Ne, Ar, Kr and Xe. It is preferable that the alkylation reaction takes place without addition of any inert gas.

The process of the present invention may be performed at atmospheric pressure or at elevated pressure. Preferably, the process of the present invention is performed at elevated pressure.

If the reaction is performed at elevated pressure, the pressure is typically in the range of 1,5 to 20 bar, preferably in the range of 2 to 15 bar, in particular in the range of 3 to 12 bar.

The present process is typically carried out at a temperature in the range of 30 to 110° C., preferably in the range of 40 to 100° C., in particular in the range of 50 to 90° C.

In a preferred embodiment of the present invention, a mixture of 1,4-bis(hydroxymethyl)cyclohexane, the inorganic base, the solvent and the phase transfer catalyst (initial mixture) is placed into a suitable reaction apparatus. The initial mixture is then stirred for a certain time (initial period), for example for 30 minutes, 1 hour or 3 hours, at the reaction temperature, as defined above. Following this, the ethyl chloride is added to the mixture of 1,4-bis(hydroxymethyl)cyclohexane, the inorganic base, the solvent and the phase transfer catalyst.

The ethyl chloride may be added in one portion or in several portions or continuously.

Typically, the ethyl chloride is used in an at least two-fold molar excess based on the amount of 1,4-bis(hydroxymethyl)cyclohexane present in the reaction mixture.

Preferably, the molar ratio of ethyl chloride to 1,4-bis(hydroxymethyl)cyclohexane is in the range of 2:1 to 15:1, more preferably in the range of 3:1 to 10:1, in particular in the range of 4:1 to 8:1.

The ethyl chloride may be added to the initial mixture, i.e. 1,4-bis(hydroxymethyl)cyclohexane, the inorganic base, the solvent and the phase transfer catalyst, in liquid or gaseous form. Preferably, the ethyl chloride is added to the initial mixture in gaseous form.

It is preferred that the initial mixture is cooled below the reaction temperature, e. g. to 5, 10 or 25° C., prior to the addition of the ethyl chloride.

After the addition of the ethyl chloride, the reaction mixture is stirred at the respective reaction temperature, as defined above, until at least 90%, preferably at least 95%, in particular at least 98%, of the bis(hydroxymethyl)cyclohexane is converted.

After completion of the reaction, the reaction mixture typically divides into two phases, i. e. a water phase and an organic phase, which can be drawn off separately. Generally, after completion of the reaction, the organic phase, comprising the 1,4-bis(ethoxymethyl)cyclohexane, can thus be separated from the water-phase by simple decantation.

In case the phase separation does not occur spontaneously through mechanical sedimentation, an organic solvent, which is not well miscible with water, may be added to the reaction mixture to increase the volume of the organic phase. Additionally or alternatively, the reaction mixture may also be subjected to liquid-liquid extraction processes that are well known to the skilled person.

After removal of the volatile organic components, such as the organic solvent, if present, or residual ethyl chloride, the 1,4-bis(ethoxymethyl)cyclohexane can typically be obtained in an acceptable purity, e.g. in a purity of at least 70 or 75%, while the mono-ethyl ether of 1,4-bis(hydroxymethyl)cyclohexane represents the major side product.

However, if necessary, the purity of the 1,4-bis(ethoxymethyl)cyclohexane obtained by the present process can be further increased by adding an additional purification step, preferably a distillation step.

Suitable distillation devices for the purification of 1,4-bis(ethoxymethyl)cyclohexane are for example distillation columns, such as tray columns optionally equipped with bubble cap trays, sieve plates, sieve trays, packages or filler materials, or spinning band columns, thin film evaporators, falling film evaporators, forced circulation evaporators, Sambay evaporators, etc. and combinations thereof.

The alkylation reaction can be designed to take place either continuously or batchwise. The batchwise alkylation can be conducted in a reaction apparatus conventionally used for reactions performed at elevated pressure, e.g. a stirred reactor, which is optionally equipped with metering devices. If the present process is carried out continuously, the reaction can be performed for example in a tube reactor or in a cascade of two or more stirred reactors, which may be back-mixed or not.

EXAMPLES

Example 1

Production of 1,4-bis(ethoxymethyl)cyclohexane from 1,4-bis(hydroxymethyl)cyclohexane with ethyl chloride Diol (18 g, 125 mmol), NaOH (35% aq., 57 g, 500 mmol) and tetra-n-butylammoniumbromide (4.02 g) were charged into an autoclave and stirred at 70° C. for 1 h. The reaction was cooled to room temperature and ethyl chloride (50.6 g, 784 mmol) was added as a gas to the vessel. The temperature was once again raised to 70° C., creating an internal pressure of 5.9-9.6 bar. After 8 h, the reaction was cooled to room temperature, the pressure was slowly released and the autoclave flushed with $N_2$.

The phases were separated and the organic phase analyzed.
Conversion: 99%
Selectivity (diether): 80%
Selectivity (monoether): 20%

Comparative Example 1

Production of 1,4-bis(ethoxymethyl)cyclohexane from 1,4-bis(hydroxymethyl)cyclohexane with diethyl sulfate Diol (15 g, 104 mmol) was dissolved in THF (30 mL) and NaOH (35% aq., 47.55 g, 416 mmol) and tetra-n-butylammoniumbromide (3.35 g) were added. The mixture was stirred at 50-52° C. for 1 h, then diethyl sulfate (2.5 eq., 40.09 g, 260 mmol) was added over 10 min. The batch was stirred for 4 h at 60° C. The reaction was cooled to room temperature, a further 30 mL THF was added and the phase separated. The organic phase was concentrated in vacuo and analyzed.
Conversion: 89%
Selectivity (diether): 45%
Selectivity (monoether): 55%

We claim:
1. A process for preparing 1,4-bis(ethoxymethyl)cyclohexane, which comprises reacting 1,4-bis(hydroxymethyl)cyclohexane with ethyl chloride in the presence of an inorganic base, a solvent and a phase transfer catalyst to yield a reaction mixture containing 1,4-bis(ethoxymethyl)cyclohexane,
   wherein the inorganic base is selected from the group consisting of alkali metal hydroxides and earth alkaline metal hydroxides, and wherein the solvent is selected from water or a mixture of water with at least one organic solvent.
2. The process of claim 1, wherein the inorganic base is selected from the group consisting of potassium hydroxide and sodium hydroxide.
3. The process according to claim 1, wherein the inorganic base is used in the form of an aqueous solution.
4. The process of claim 1, wherein the molar ratio of $OH^-$ in the inorganic base to 1,4-bis(hydroxymethyl)cyclohexane is in the range of 2:1 to 20:1.
5. The process of claim 1, wherein the molar ratio of ethyl chloride to 1,4-bis(hydroxymethyl)cyclohexane is in the range of 2:1 to 15:1.
6. The process of claim 1, wherein said at least one organic solvent is selected from the group consisting of aliphatic hydrocarbons, aromatic hydrocarbons, aliphatic ethers, alicyclic ethers and mixtures thereof.

7. The process of claim 1, wherein the solvent comprises at least 90% by weight, of water based on the total amount of solvent.

8. The process of claim 1, wherein the phase transfer catalyst is selected from quaternary ammonium salts.

9. The process of claim 1, wherein the phase transfer catalyst is selected from tetra-($C_1$-$C_{10}$-alkyl)ammonium salts.

10. The process of claim 1, wherein the amount of the phase transfer catalyst used is in the range of 1 to 20 mol-%, based on the amount of 1,4-bis(hydroxymethyl)cyclohexane.

11. The process of claim 1, wherein the ethyl chloride is added to a mixture of 1,4-bis(hydroxymethyl)cyclohexane, the inorganic base, the solvent and the phase transfer catalyst.

12. The process of claim 1, wherein the reaction is performed at a temperature in the range of 30 to 110° C.

13. The process of claim 1, further comprising purifying the reaction mixture containing 1,4-bis(ethoxymethyl)cyclohexane.

14. The process of claim 1, wherein the phase transfer catalyst is tetra-n butylammonium salts.

\* \* \* \* \*